United States Patent [19]
Curtis et al.

[11] Patent Number: 5,412,221
[45] Date of Patent: May 2, 1995

[54] PARTICLE FALLOUT/ACTIVITY SENSOR

[75] Inventors: Ihlefeld M. Curtis, Orlando; Robert C. Youngquist, Cocoa; John S. Moerk; Kenneth A. Rose, III, both of Titusville, all of Fla.

[73] Assignee: The United States of America as represented by the Administrator of the National Aeronautics and Space Administration, Washington, D.C.

[21] Appl. No.: 233,584

[22] Filed: Apr. 26, 1994

[51] Int. Cl.$^6$ ............................................. G01N 15/06
[52] U.S. Cl. ...................................... 250/573; 356/338
[58] Field of Search ............... 250/571, 573, 574, 221, 250/222.1, 222.2; 356/338, 342

[56] References Cited

U.S. PATENT DOCUMENTS

| | | |
|---|---|---|
| 3,222,925 | 12/1965 | Kracke et al. |
| 3,475,965 | 11/1969 | Koblin et al. |
| 3,702,734 | 11/1972 | Lindahl et al. |
| 4,254,414 | 3/1981 | Street et al. |
| 4,748,336 | 5/1988 | Fujie et al. ........................ 250/573 |
| 4,825,094 | 4/1989 | Borden et al. |
| 4,966,457 | 10/1990 | Hayano et al. |
| 5,076,692 | 12/1991 | Neukermans et al. |
| 5,166,537 | 11/1992 | Horiuchi et al. .................. 250/573 |
| 5,245,403 | 9/1993 | Kato et al. |

*Primary Examiner*—David C. Nelms
*Assistant Examiner*—John R. Lee
*Attorney, Agent, or Firm*—William J. Sheehan; Guy M. Miller; Alan J. Kennedy

[57] ABSTRACT

A particle fallout/activity sensor measures relative amounts of dust or other particles which collect on a mirror in an area to be monitored. The sensor includes a sensor module and a data acquisition module, both of which can be operated independently of one another or in combination with one another. The sensor module includes a housing containing the mirror, an LED assembly for illuminating the mirror and an optical detector assembly for detecting light scattered off of the mirror by dust or other particles collected thereon. A microprocessor controls operation of the sensor module's components and displays results of a measurement on an LCD display mounted on the housing. A push button switch is also mounted on the housing which permits manual initiation of a measurement. The housing is constructed of light absorbing material, such as black delrin, which minimizes detection of light by the optical detector assembly other than that scattered by dust or particles on the mirror. The data acquisition module can be connected to the sensor module and includes its own microprocessor, a timekeeper and other digital circuitry for causing the sensor module to make a measurement periodically and send the measurement data to the data acquisition module for display and storage in memory for later retrieval and transfer to a separate computer. The time tagged measurement data can also be used to determine the relative level of activity in the monitored area since this level is directly related to the amount of dust or particle fallout in the area.

20 Claims, 5 Drawing Sheets

PARTICLE FALLOUT/ACTIVITY SENSOR

ORIGIN OF THE INVENTION

The invention described herein was made in the performance of work under a NASA contract and is subject to the provisions of Public Law 96-517 (35 USC 202) in which the contractor has elected not to retain title.

BACKGROUND OF THE INVENTION

The present invention relates to a particle fallout/activity sensor which can monitor particle fallout in an area over a period of time at specified intervals, and store the fallout data in memory for later recall and analysis.

Detection and measurement of particle fallout, e.g. dust, fibers, etc., onto sensitive payload components is an ongoing part of payload processing at the Kennedy Space Center. At present, an indication of the amount and type of particle contamination is achieved by the use of witness plates. These plates are placed at selected locations around payload components and left for a period of time to collect fallout. The plates are then removed to a laboratory and examined under a microscope to determine and tabulate the amount and types of particles that have accumulated. This approach has the benefit of allowing a trained operator to examine the dust visually and provide an accurate analysis, but is time consuming and provides no indication of when contamination occurs. Unfortunately, the risk of payload damage from undetected contamination events is a very real possibility and the witness plate approach does not allow potentially destructive contamination events to be detected since it restricts fallout measurements to an accumulated account over an extended period of time.

A need therefore exists for a particle fallout monitoring system which provides information not only on the amount of particle fallout occurring over a predetermined time interval, but also information on the time at which the particle fallout occurs.

SUMMARY OF THE INVENTION

The present invention satisfies the foregoing need by providing a particle fallout sensor which monitors particle fallout over a period of time at specified intervals, and can store both the magnitude and time of occurrence of the sensed particle fallout in memory. The time of occurence information is valuable for two reasons. First, it enables a correlation with outside events to be established. In this manner, the sensor can also be employed as an activity sensor since more particle fallout is known to occur during periods of high activity and movement in the sensor area than during periods of little or no activity or movement. Second, the time of occurrence information enables fallout rate calculations to be made by calculating the difference in the total accumulated fallout from one measurement interval to the next. This information can be employed to detect and flag undesired contamination events, thereby allowing for immediate corrective action.

Broadly, the present invention provides a particle fallout/activity sensor which includes a microprocessor controlled sensor module that detects particle accumulation on a sensor surface, such as a mirror, and converts this information into digital data that can either be displayed directly or transmitted to a separate data acquisition module. The data acquisition module includes a microprocessor and a timekeeper with a memory. When the data acquisition module is connected to the sensor module, it periodically requests the sensor module to make a measurement, convert the measurement to digital data and send it to the data acquisition module which stores the received measurement data in the timekeeper's memory. The timekeeper is employed to initiate the periodic measurement request and to time tag the received measurement data. The stored information can be later downloaded from the memory to a separate computer for an analysis of the particle fallout data.

In the preferred embodiment of the present invention, the sensor module employs an optical particle sensing system which includes a mirror for accumulating dust or other particles, an infrared LED to illuminate a portion of the mirror, and an optical detector assembly to detect light being scattered off of the mirror by particles accumulated thereon. The mirror is contained within a housing constructed of light absorbing material and designed in such a manner that minimal scattered light from surfaces other than the mirror, as well as minimal outside light, can reach the optical detector assembly. The optical detector assembly generates a signal which is digitized, processed and displayed on an LCD on top of the sensor module. In addition, if the sensor module is connected to the data acquisition module, the digitized signal is also transmitted to the data acquisition unit via a serial communications interface.

Preferably, both the sensor module and the data acquisition module are battery powered for portability. In addition, both modules are capable of independent operation. When the sensor module is in this mode of operation, actuation of a momentary contact push button switch causes the sensor module to take a reading, and display a number proportional to the amount of scattered light received by the detector assembly. The data acquisition module is capable of independent operation in that it can be turned on unattached to any other unit and information will be displayed indicating the module's current configuration, i.e., the main memory, current time, turn-on time, time interval, calibration values, etc. However, recall and display of stored measurement data can only be carried out by interfacing the data acquisition module with a separate computer. When the sensor module is connected to the data acquisition module, power is supplied to both modules by the battery contained within the data acquisition module.

The sensor module also includes circuitry which helps remove background signals and improves the sensitivity of the detector assembly. In particular, the sensor module circuitry causes the LED to be turned off and on several thousand times during each sampling interval. The resulting signal difference at the detector assembly between on and off states of the LED is then averaged to produce a relatively low noise signal.

BRIEF DESCRIPTION OF THE DRAWINGS

The foregoing and additional features and advantages of the present invention will become apparent from the following detailed description of a preferred embodiment thereof, taken in conjunction with the accompanying drawings in which.

DETAILED DESCRIPTION OF A PREFERRED EMBODIMENT

Figure 1:
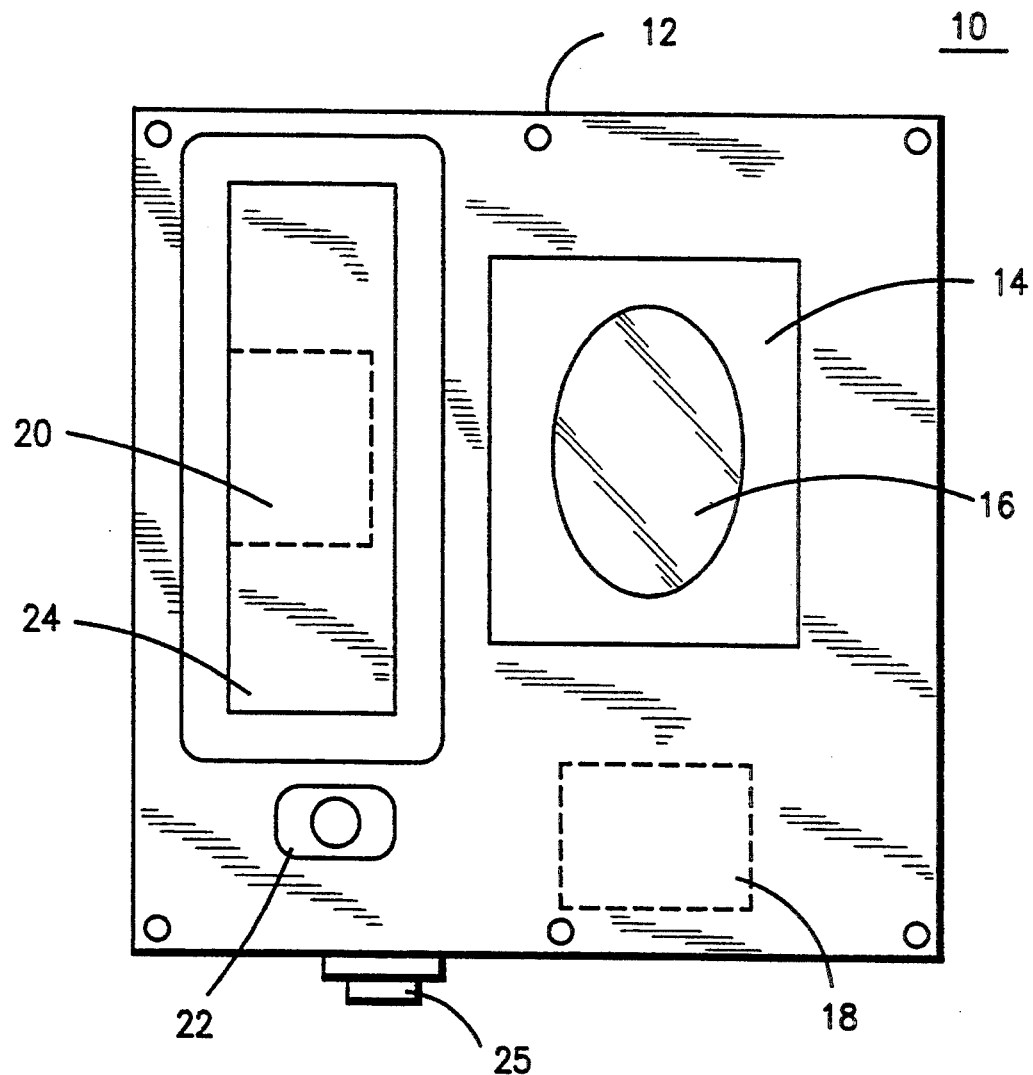
FIG. 1 is a schematic illustration of the mechanical and electrical components which make up a sensor module constructed in accordance with the preferred embodiment of the invention.

Turning now to a more detailed consideration of a preferred embodiment of the present invention, FIG. 1 shows a particle fallout sensor module 10 which includes a housing 12 that is preferably constructed of a light absorbing material, such as black delrin. Disposed in the top of the housing 12 is a aperture 14 through which dust or other particles can fall and settle onto an oval shaped test mirror 16 contained inside the housing 12.

Also contained within the housing 12, as indicated by the dashed lines in FIG. 1, are an LED assembly 18 and an optical detector assembly 20. As discussed in greater detail below in conjunction with FIGS. 2 and 3, the LED assembly 18 generates the optical signal needed to measure the dust and other particles which settle onto the mirror 16, and the optical detector assembly 20 measures the amount of light scattered by these particles.

Disposed on top of the housing 12 is a momentary contact push button switch 22 which actuates the sensor module circuitry contained within the housing 12 (discussed below and illustrated in FIG. 4), and causes the sensor module 10 to make a particle fallout measurement. The results of the measurement are digitized and displayed on an LCD display 24 which is also disposed on top of the housing 12. The measurement data can also be transmitted to a separate data acquisition module (discussed below in conjunction with FIG. 5) via an electrical connector 25 and a ribbon cable (not shown).

Figure 2:
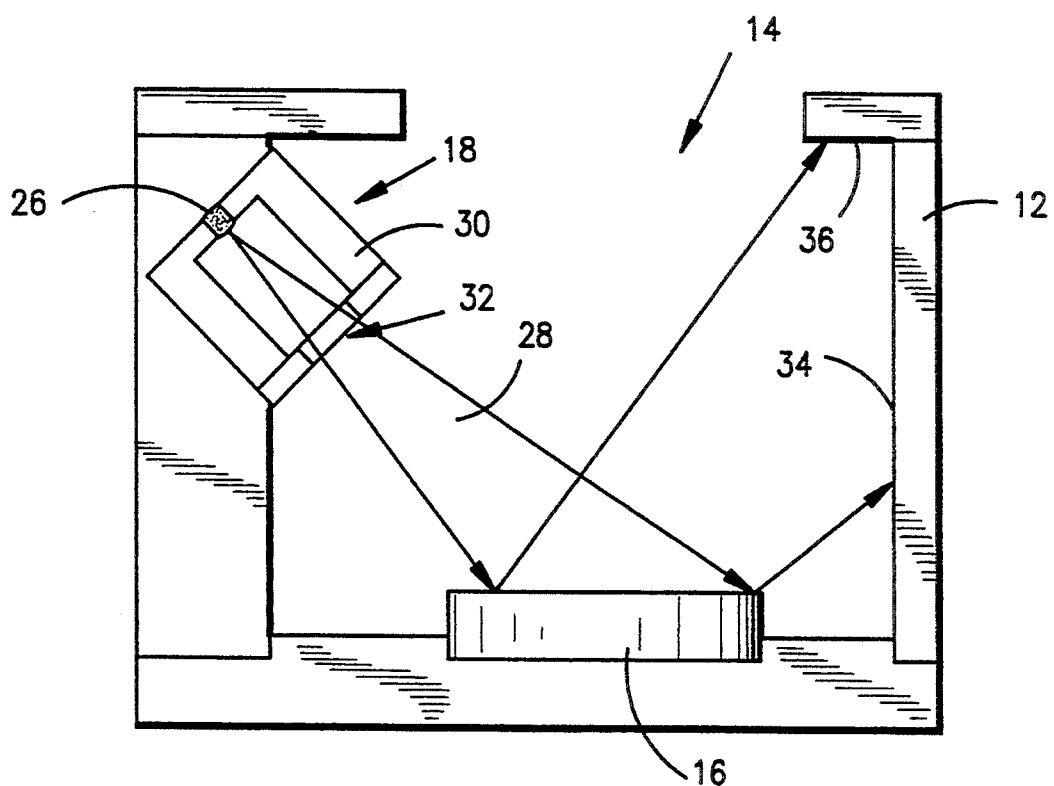
FIG. 2 is a schematic cross sectional side view of the sensor module showing the relative positions of a particle collecting mirror and an LED assembly for illuminating the mirror.

FIG. 2 illustrates the relative positioning of the LED assembly 18 and the mirror 16 within the housing 12. The LED assembly 18 includes an infrared LED 26 which has a clear lens formed integrally therewith so that most of the infrared radiation is emitted into a relatively narrow forward cone shaped beam 28. The infrared LED 26 is contained within an opaque housing 30 having a limiting aperture 32 formed in one end thereof which further constrains the beam 28 of radiation so that substantially all of it is directed onto the surface of the mirror 16. Without the housing 30 and aperture 32, some of the radiation emitted by the LED 26 would not hit the mirror 16 and could scatter within the housing 12, possibly reaching the optical detector assembly 20 and thereby producing erroneous signals.

The LED assembly 18 is therefore designed to illuminate the mirror 16 fully with infrared radiation. If no dust, scratches or other particles are present, this radiation will reflect off of the mirror 16 and be directed as indicated by the arrows in FIG. 2 against a side wall 34 and a top wall 36 of the housing 12 which absorb most of the reflected illumination since they are made of black delrin, or other light absorbing material. As illustrated in FIG. 1, the optical detector assembly 20 is positioned at an angle perpendicular to the path along which the beam 28 of infrared radiation travels from the LED assembly 18 to the mirror 16. This positioning, along with the use of the light absorbing black delrin in the housing 12, insures that minimal scattered light from surfaces other than the mirror 16 can reach the optical detector assembly 20. This is important because allowing scattered light from surfaces other than the mirror 16 to reach the optical detector assembly 20 can cause two problems. First, a potentially large offset signal on the detector to compensate for the detection of unwanted scattered light can reduce the dynamic range of the instrument (note that this is also one reason why a mirror is used as the dust collection surface rather than an arbitrary material). Second, small changes in this scattered light signal would be interpreted by the detector as changes in the amount of dust or other particles on the mirror 16.

Figure 3:
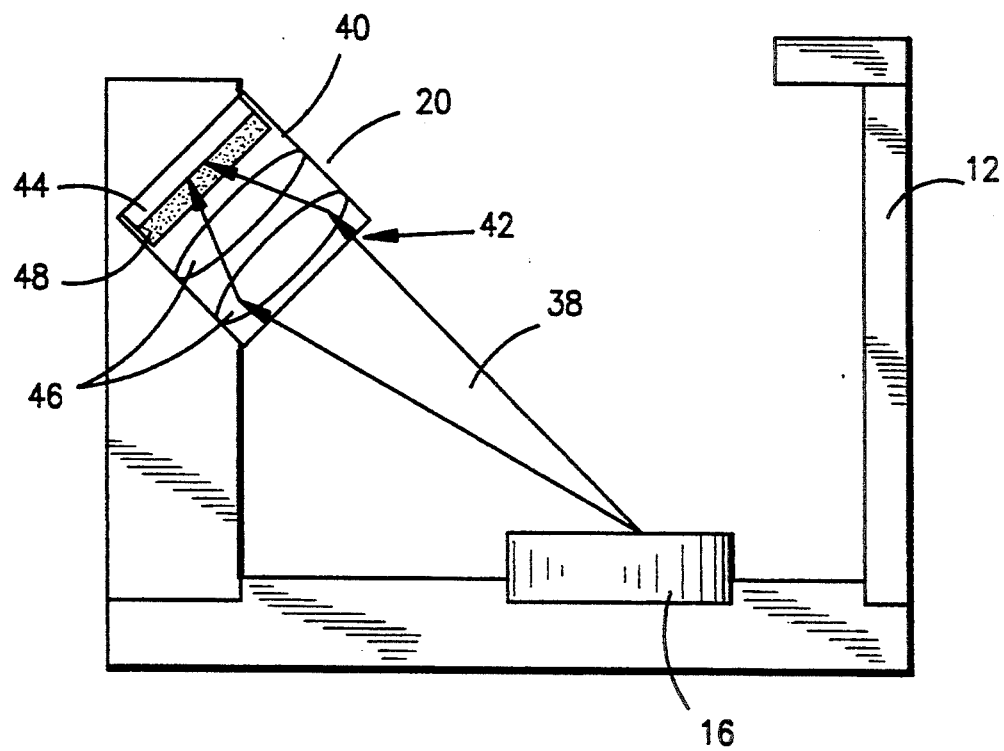
FIG. 3 is a schematic cross sectional side view of the sensor module showing the relative positions of the mirror and an optical detector assembly for detecting light reflected off of the mirror.

If dust or other particles fall through the aperture 14 onto the surface of the mirror 16, some of the infrared radiation from the LED 26 will be scattered by the dust or other particles in all directions. As illustrated in FIG. 3, a portion 38 of these dust scattered rays will enter the optical detector assembly 20. The optical detector assembly 20 is also designed to maximize its sensitivity to light scattered off of the mirror 16 and to minimize its sensitivity to all other light sources. In particular, the optical detector assembly 20 includes an opaque housing 40 having an aperture 42 disposed in a bottom end for reception of these dust scattered rays 38, and a large area silicon photodetector 44 disposed at an opposite top end thereof. A pair of glass lenses 46 are positioned within the housing 40 that limit the field of view of the photodetector 44 to the surface area of the mirror 16, and thereby help prevent light from other areas from reaching the photodetector 44. They also aid in collecting the light that is scattered by the mirror 16 to improve the response of the optical detector assembly 20. Finally, an infrared filter 48 is positioned between the lenses 46 and the photodetector 44 which helps insure that the photodetector 44 will be responsive only to the infrared radiation emitted by the LED assembly 18 and scattered off of the mirror 16.

Figure 4:
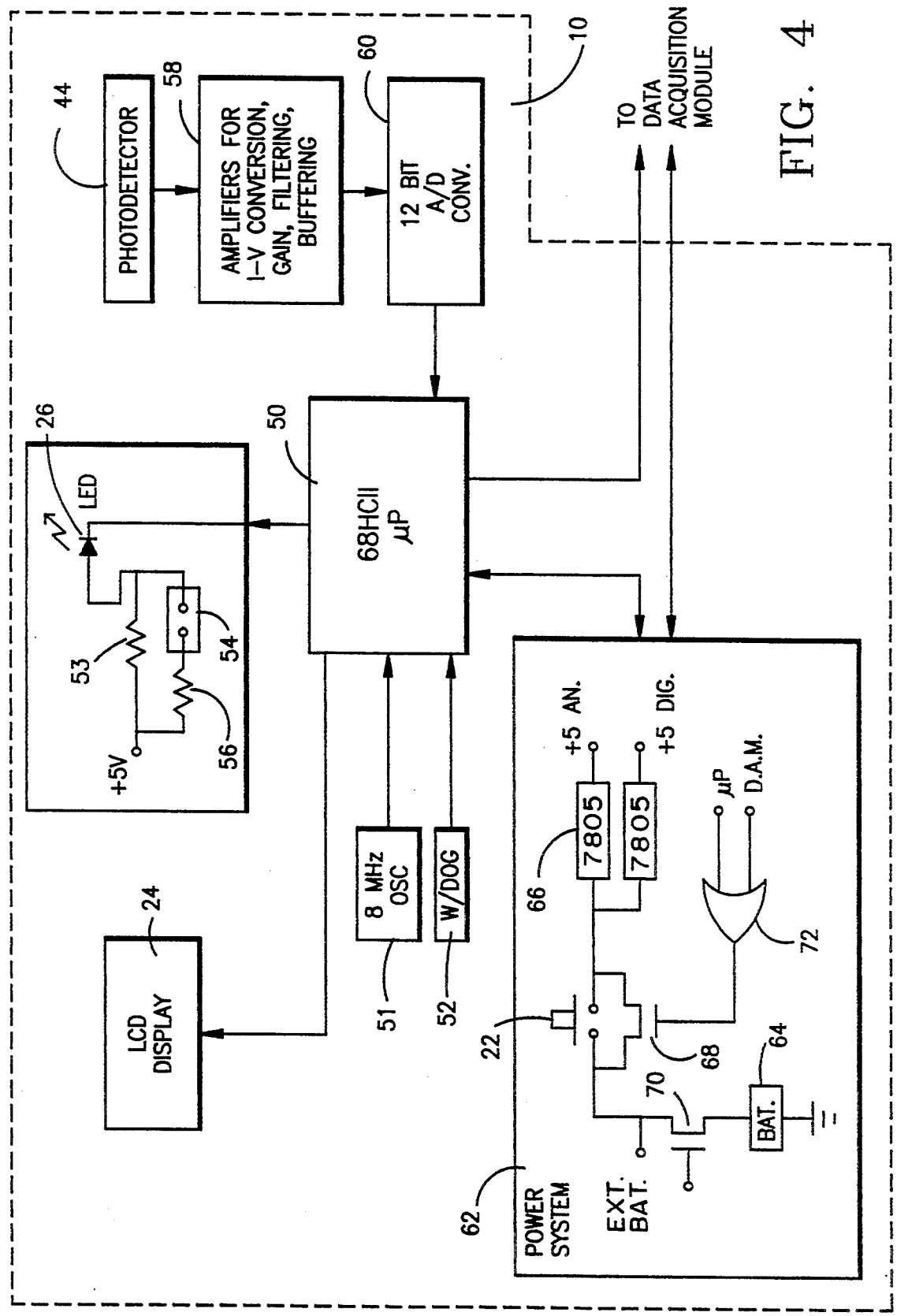
FIG. 4 is a schematic block diagram of the electrical circuitry contained within the sensor module of the preferred embodiment.

FIG. 4 shows the electrical circuitry contained within the sensor module 10 which performs the particle or dust fallout measurements and generates digital signals corresponding thereto. The heart of the circuit is a conventional 68HC11 microprocessor 50 which controls the sensor module 10, performs signal processing and enables communication with a separate data acquisition module as discussed below in conjunction with FIG. 5. Connected to the microprocessor 50 is conventional processor support circuitry including an 8 MHz oscillator 51 and a watchdog circuit 52.

The microprocessor 50 is connected to, and controls operation of, the LED 26. A simple sensitivity adjustment circuit is provided to change the optical power of the LED 26. This circuit comprises a first resistor 53 connected in series between a 5 volt voltage source and the LED 26, and a jumper connection 54 which enables a second resistor 56 to be selectively inserted in parallel with the first resistor 53 through use of a jumper wire (not shown).

The photodetector 44 generates an analog current output which is fed through a plurality of amplifier stages 58 that provide current-to-voltage conversion, gain, high and low pass filtering and buffering. The final output from the amplifier stages 58 is digitized in a conventional 12 bit analog to digital converter 60, and the resulting digitized signals are then fed to the microprocessor 50. The microprocessor 50 then outputs the result of the data measurement to the LCD display 24. In addition, if a separate data acquisition module is connected to the sensor module 10, the microprocessor 50 sends it the measurement data.

A power system 62 is provided which supplies power to all of the electrical components in the sensor module 10. The power system 62 includes a conventional 9 volt battery 64, the momentary contact push button switch 22 and a pair of LM7805 voltage regulator circuits 66 for supplying two 5 volt outputs, one for the digital components and the other for the analog components of the sensor module 10. Power can also be supplied to the power system 62 from an external battery or other power supply located in a data acquisition module when the sensor module 10 is connected thereto. The power system 62 allows turn-on of the sensor module 10 from the push button switch 22 or a remotely located data acquisition module connected thereto. The microprocessor 50 is also programmed to turn off the sensor module 10 after either displaying a measurement result on the LCD display 24 or sending the result to a data acquisition module.

These functions are accomplished through use of a pair of MOSFET switches 68 and 70 and an OR gate or similar circuit 72. The first switch 68 connects either the battery 64 or the external battery to the voltage regulator circuit 66 when it receives a signal from the OR gate 72 either from the microprocessor 50 or a connected data acquisition module. When the momentary push button switch 22 is actuated to temporarily jump across the first switch 68, this powers up the microprocessor 50 which then maintains the power up condition by sending a signal to the OR gate 72. Once a measurement has been completed, the power-on signal is no longer sent to the OR gate 72 and the first switch 68 is opened, thereby turning off the power system 62. The second switch 70 is remotely actuated to disconnect the battery 64 from the power system circuit when the external battery is connected thereto.

Figure 5:
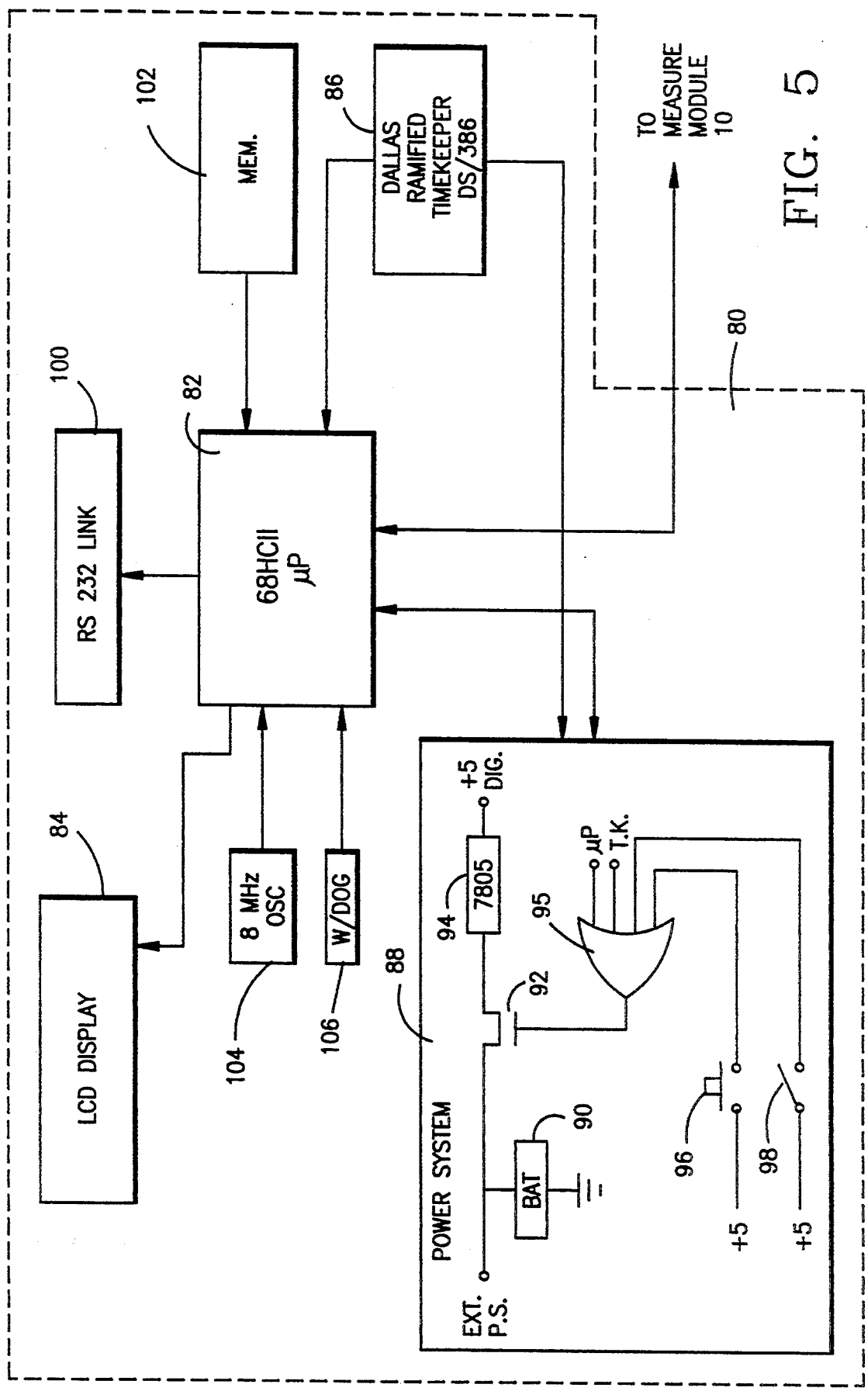
FIG. 5 is a schematic block diagram of the circuitry of a data acquisition module of the preferred embodiment; and, FIG. 6 is a flow chart of the operational steps carried out by the sensor during operation with the data acquisition module.

Turning now to FIG. 5, the circuitry of a data acquisition module 80 which can be interfaced to the sensor module 10 is illustrated. Like the sensor module 10, the heart of the data acquisition module 80 is a 68HC11 microprocessor 82. The data acquisition module 80 is employed to acquire particle fallout measurement data from the sensor module 10 at specified intervals on a continuing basis. As discussed below, this data is displayed when acquired and stored in memory for later transferal to a remote computer. An LCD display 84 is connected to the microprocessor 82 for displaying the measurement data and other information including measurement stop time and date, number of samples left to be measured, calibration data, unit number, etc.

A Dallas ramified timekeeper 86, which by way of example can be a model DS1386, is connected to the microprocessor 82 which tells the microprocessor 82 when to turn on the sensor module 10 to initiate a measurement, and also includes memory in which the resulting measurement data is stored when it is received from the sensor module 10. The data is also time tagged by the timekeeper 86 when it is stored so that the time of occurrence of each measurement is also recorded.

Like the sensor module 10, the data acquisition module 80 also includes a power system 88. The power system 88 includes a rechargeable battery 90 which is selectively connected by a MOSFET switch 92 to a conventional LM7805 voltage regulator circuit 94 that generates a 5 volt output for powering each of the digital circuits in the data acquisition module 80. The MOSFET switch 92 is actuated through a 4 input OR gate 95 which receives inputs from the timekeeper 86, the microprocessor 82, a momentary push button switch 96 and an on/off switch 98, the later two being disposed on the data acquisition module's housing (not shown). The momentary push button switch 96 is provided so that an operator can interrogate the system status while it is in operation. For example, if the system is acquiring data on 30 minute intervals, an operator might want to know the status of the system without having to wait for the data acquisition module 80 to turn itself on. This can be done by pressing the push button switch 96 which will turn on the data acquisition module 80 (not the sensor module 10) and allow the operator to toggle through several screens of information showing the current system status, i.e., how much memory is left, the last measurement value, the time interval, etc. The on/off switch 98 is provided so that when the data acquisition module 80 is first turned on, it will display its configuration showing that it is operating and set up properly. An external power supply or battery charger can also be selectively connected across the battery 90.

A number of other conventional circuit elements are also connected to the microprocessor 82. These include an RS-232 serial data link 100 which enables the data acquisition module 80 to be connected to another computer for transfer of acquired data from the timekeeper 86 and for setting of calibration values. A memory 102 is connected to the microprocessor 82 which stores the system operational microcode. Finally, processor support circuitry is connected to the microprocessor 82 which includes an 8 MHz oscillator 104 and a watchdog circuit 106.

The operation of the sensor module 10 both in a stand alone mode and when it is connected to the data acquisition module 80 will now be discussed. In the stand alone mode, the sensor module 10 is actuated manually by pressing the push button switch 22 momentarily. This connects the battery 64 to the voltage regulator circuits 66 and causes the microprocessor 50 to initiate a reading and send a signal to the OR gate 72 to maintain power to the module circuitry. During the reading, the microprocessor 50 is programmed to turn the LED 26 on and off rapidly at a frequency of approximately a few kilohertz. The resulting signals generated by the photodetector 44 and fed in digital form by the A/D converter 60 to the microprocessor 50 are then processed to separate out background light and noise from the detected signals. This is accomplished by determining the difference between the detected signals when the LED 26 is switched on and when it is switched off and averaging these differences. This process is a conventional synchronous detection scheme which provides rejection of background light, reduction of noise through averaging and reduction of 1/f noise. The computed measurement data is then displayed on the LCD display 24. Finally, the microprocessor 50 ceases sending the signal to the OR gate 72 to turn off the sensor module 10. The complete measurement process including turn-on, stabilization, measurement, display and turn-off typically occurs in under 5 seconds.

Figure 6:
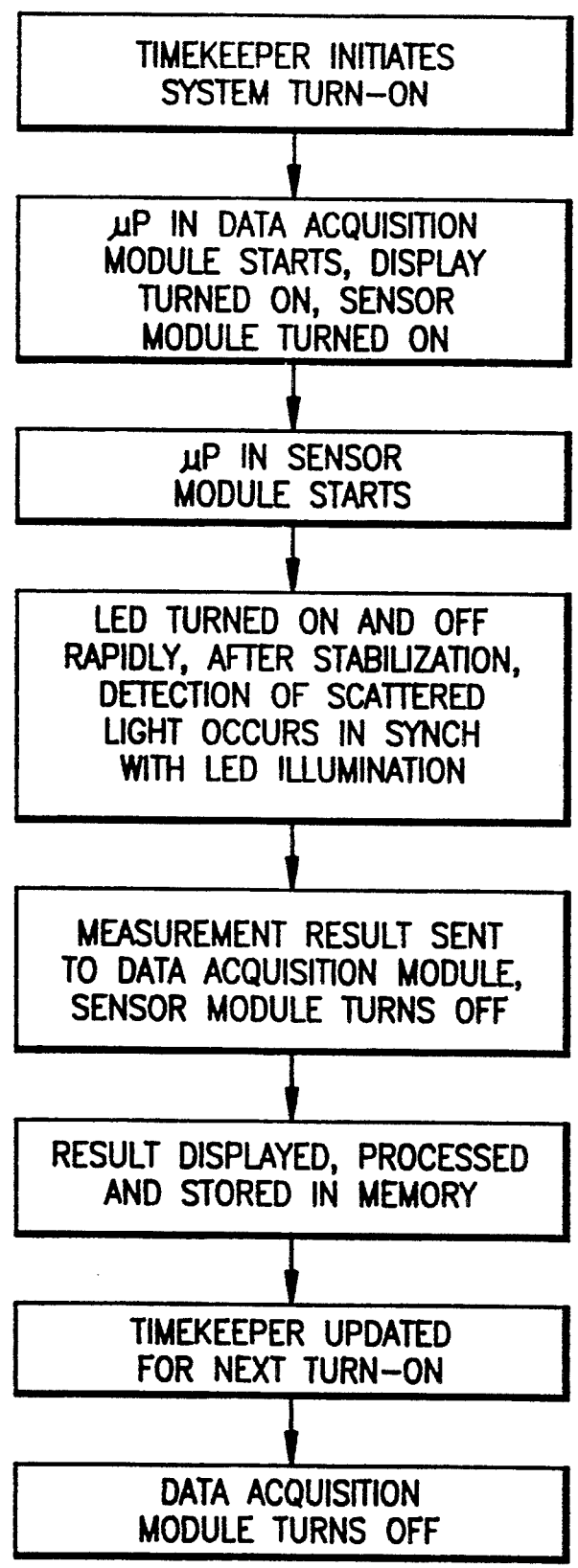

When the data acquisition module 80 is connected to the sensor module 10 for autonomous operation, the timekeeper 86 initiates system turn-on as illustrated in the flow chart of FIG. 6. This is accomplished by programming the timekeeper 86 to send a turn-on request signal to the power system 88 at programmed times to turn on all of the associated circuit elements in the data acquisition module 80. When the microprocessor 82 in the data acquisition module 80 turns on, it sends a signal to the power system 62 of the sensor module 10, thereby causing the sensor module 10 to turn on also. The microprocessor 50 in the sensor module 10 then starts executing its measurement program in the manner discussed previously by actuating the LED 26 and acquiring a measurement from the photodetector 44. The measurement data is sent back to the data acquisition module 80 where it is displayed on the LCD display 84, processed using calibration values to determine the amount of particle fallout and stored in memory in the timekeeper 86 for later retrieval. During processing, the microprocessor's software can detect when an undesirable fallout or contamination level has been reached and flag this condition on the display 84 or by way of any other suitable visual or audio alarm indicator. After storage of the measurement data, the ramified timekeeper 86 is then updated by the microprocessor 82 for the next turn-on and measurement cycle. Finally, the microprocessor 82 turns off the power system 62 in the sensor module 10 and the power system 88 in the data acquisition module.

Although the present invention has been described in terms of a preferred embodiment, it will be understood that numerous modifications and variations could be made thereto without departing from the scope of the invention as set forth in the following claims.

What is claimed is:

1. Apparatus for sensing particle fallout comprising a sensor module, said sensor module including:
   a) a housing having an aperture in a top side thereof and an interior;
   b) a reflective surface positioned within said housing for receiving particle fallout through said aperture from an area to be monitored;
   c) illuminating means positioned in the interior of said housing for illuminating said reflective surface with a beam of electromagnetic radiation;
   d) an electromagnetic radiation responsive detector positioned in the interior of said housing for receiving electromagnetic radiation scattered off of particles collected on said reflective surface, said detector generating an electrical output having a magnitude proportional to the amount of particles collected on said reflective surface;
   e) an A/D converter for converting said electrical output to a digital signal;
   f) a sensor module microprocessor for controlling operation of said illuminating means and said detector, and receiving said digital signal from said A/D converter; and,
   g) a display disposed on said housing and connected to said microprocessor for receiving and displaying said digital signal.

2. The apparatus of claim 1, wherein said reflective surface comprises a mirror.

3. The apparatus of claim 1, wherein said housing is constructed of light absorbing material.

4. The apparatus of claim 3, wherein said light absorbing material is black delrin.

5. The apparatus of claim 1, wherein said illuminating means comprises an infrared LED.

6. The apparatus of claim 5, wherein said electromagnetic radiation responsive detector comprises a photodetector array and an infrared filter disposed between said reflective surface and said photodetector array so that said photodetector array receives only electromagnetic radiation scattered off of said reflective surface from said infrared LED.

7. The apparatus of claim 1, wherein said electromagnetic radiation responsive detector is positioned at an angle perpendicular to a beam path along which a beam of electromagnetic radiation travels from said illuminating means to said reflective surface.

8. The apparatus of claim 1, further including:
   h) a power system for supplying power to said illuminating means, said detector, said A/D converter, said microprocessor and said display; and,
   i) a switch for selectively actuating said power system.

9. The apparatus of claim 8, wherein said switch is controlled by said microprocessor so that said microprocessor maintains actuation of the power system during a fallout measurement, and deactivates the power system after a measurement has been completed and displayed.

10. The apparatus of claim 9, further including a momentary contact push button switch connected across said power system switch for initiating actuation of said power system.

11. The apparatus of claim 1, further including:
   a data acquisition module connectable to said sensor module, said data acquisition module comprising:
   a) a data acquisition module microprocessor connectable to said sensor module; and,
   b) a timekeeper connected to said data acquisition module microprocessor for periodically signalling said data acquisition module microprocessor to cause said sensor module to make a particle fallout measurement and transmit the resulting measurement data to a memory in said timekeeper.

12. The apparatus of claim 11, wherein said data acquisition module further includes:
   c) a power system for supplying power to said data acquisition module microprocessor and said timekeeper; and,
   d) a power system switch for selectively controlling actuation of said power supply.

13. The apparatus of claim 12, wherein said timekeeper and said data acquisition module microprocessor are connected to said power system switch so that said timekeeper initiates actuation of said power system and said data acquisition module microprocessor maintains actuation of said power system during a fallout measurement by said sensor module, and deactuates said power system after a measurement is completed.

14. The apparatus of claim 13, wherein said power system is also connectable to said sensor module illuminating means, detector, A/D converter, microprocessor and display to supply power thereto.

15. The apparatus of claim 1, wherein said sensor module microprocessor further includes means to flash said illuminating means on and off rapidly, determine the difference between the electrical output of said detector when the illuminating means is on and when it is off, and average the difference to reduce noise effects.

16. Apparatus for sensing particle fallout comprising:
a sensor module, said sensor module including:
- a) a fallout detector system for detecting particle fallout on a surface and generating a digital signal corresponding to the amount of particle fallout on the surface; and,
- b) a sensor module microprocessor for controlling operation of said system and receiving said digital signal from said system; and a data acquisition module connectable to said sensor module, said data acquisition module comprising:
- a) a data acquisition microprocessor connectable to said sensor module microprocessor; and,
- b) a timekeeper connected to said data acquisition microprocessor for periodically signalling said data acquisition microprocessor to cause said sensor module to make a particle fallout measurement and transmit the resulting measurement data to a memory in said timekeeper.

17. The apparatus of claim 16, wherein said sensor module further includes:
- c) a sensor module power system for supplying power to said system and said sensor module microprocessor; and,
- d) a sensor module power system switch for selectively actuating said sensor module power system, said sensor module power system switch being selectively actuatable either by said sensor module microprocessor or said data acquisition module microprocessor.

18. The apparatus of claim 17, wherein said sensor module power system further includes a momentary contact push button switch connectable across said sensor module power system switch for initiating actuation of said sensor module power system.

19. The apparatus of claim 17, wherein said data acquisition module further includes:
- c) a data acquisition module power system; and,
- d) a data acquisition module power system switch for selectively actuating said data acquisition module power system, said data acquisition module power system switch being connected to said data acquisition module microprocessor and said timekeeper so that said timekeeper can initiate actuation of said data acquisition module power system and said data acquisition module microprocessor can maintain actuation of said data acquisition power system during a particle fallout measurement, and deactivate said data acquisition module power system after a measurement is complete.

20. The apparatus of claim 16, wherein said data acquisition module microprocessor includes means to detect and flag an undesirable level of particle fallout measured by said sensor module.

* * * * *